United States Patent
Zaidi et al.

(10) Patent No.: US 12,280,253 B2
(45) Date of Patent: *Apr. 22, 2025

(54) ELECTRODE DEVICES FOR NEUROSTIMULATION

(71) Applicant: Galvani Bioelectronics Limited, Brentford (GB)

(72) Inventors: Faisal Zaidi, Brentford (GB); Sabastien Ouchouche, Brentford (GB); Paul Matteucci, Brentford (GB)

(73) Assignee: GALVANI BIOELECTRONICS LIMITED, Stevenage (GB)

( * ) Notice: Subject to any disclaimer, the term of this patent is extended or adjusted under 35 U.S.C. 154(b) by 563 days.

This patent is subject to a terminal disclaimer.

(21) Appl. No.: 17/248,735

(22) Filed: Feb. 5, 2021

(65) Prior Publication Data

US 2021/0178153 A1 Jun. 17, 2021

Related U.S. Application Data

(63) Continuation of application No. 16/619,396, filed as application No. PCT/GB2018/052076 on Jul. 23, 2018, now Pat. No. 10,946,189.

(Continued)

(51) Int. Cl.
*A61N 1/05* (2006.01)
*A61K 9/00* (2006.01)
(Continued)

(52) U.S. Cl.
CPC .......... *A61N 1/0556* (2013.01); *A61K 9/0024* (2013.01); *A61K 31/56* (2013.01);
(Continued)

(58) Field of Classification Search
CPC .... A61N 1/0556; A61N 1/3605; A61N 1/375; A61N 1/0558; A61K 9/0024; A61K 31/56
See application file for complete search history.

(56) References Cited

U.S. PATENT DOCUMENTS 4,920,979 A * 5/1990 Bullara ................ A61N 1/0556
607/118
5,143,067 A * 9/1992 Rise ..................... A61N 1/0556
600/377
(Continued)

FOREIGN PATENT DOCUMENTS

CN 101048194 A 10/2007
CN 101198372 A 6/2008
(Continued)

OTHER PUBLICATIONS

Chinese Office Action received for CN Application No. 201880063209.9 on Mar. 29, 2023, 9 pgs.
(Continued)

*Primary Examiner* — Catherine M Voorhees
*Assistant Examiner* — James Moss
(74) *Attorney, Agent, or Firm* — Merchant & Gould P.C.

(57) ABSTRACT

An extravascular or intravascular neural interface is disclosed comprising three C-ring portions, with at least two including an electrode, an electrode pair or an electrode array. The portions are formed of a flexible material that is configured to enable the portions to self-size to fit around or against a surface of a target vessel when the neural interface is released at a position along the target vessel. A spinal portion configured to house electrical conductors for the electrodes is connected to one or more portions. The portions may be spaced sufficient apart to permit radial expansion and contraction of a target vessel around or within which the neural interface is placed, to reduce never compression, open trench low-pressure unrestricted blood-flow, and to enhance fluid exchange with the target vessel. The portions may be arranged in a low helix angle forming at least two full turns.

20 Claims, 9 Drawing Sheets

Related U.S. Application Data

(60) Provisional application No. 62/692,426, filed on Jun. 29, 2018, provisional application No. 62/608,386, filed on Dec. 20, 2017, provisional application No. 62/538,359, filed on Jul. 28, 2017.

(51) Int. Cl.
*A61K 31/56* (2006.01)
*A61N 1/36* (2006.01)
*A61N 1/375* (2006.01)

(52) U.S. Cl.
CPC ......... *A61N 1/0558* (2013.01); *A61N 1/3605* (2013.01); *A61N 1/375* (2013.01)

(56) References Cited

U.S. PATENT DOCUMENTS

| | | | |
|---|---|---|---|
| 7,925,352 B2 | 4/2011 | Stack | |
| 8,155,757 B1 | 4/2012 | Niesz | |
| 8,755,907 B2 | 6/2014 | Kieval | |
| 8,855,767 B2 | 10/2014 | Faltys | |
| 9,216,280 B1 | 12/2015 | Hakki | |
| 9,283,379 B2 | 3/2016 | True | |
| 10,946,189 B2 * | 3/2021 | Zaidi | A61K 9/0024 |
| 2008/0147158 A1 * | 6/2008 | Zweber | A61N 1/0534 |
| | | | 607/122 |
| 2012/0053577 A1 * | 3/2012 | Lee | A61B 18/1815 |
| | | | 606/33 |
| 2014/0094887 A1 | 4/2014 | True | |
| 2014/0188202 A1 * | 7/2014 | Zarembo | A61N 1/0556 |
| | | | 607/118 |
| 2014/0228905 A1 * | 8/2014 | Bolea | A61F 5/566 |
| | | | 607/42 |
| 2016/0296747 A1 | 10/2016 | Glenn | |

FOREIGN PATENT DOCUMENTS

| | | | | |
|---|---|---|---|---|
| CN | 101234226 A | 8/2008 | | |
| CN | 103167892 A | 6/2013 | | |
| CN | 104353181 A | 2/2015 | | |
| EP | 0865800 A2 | 9/1998 | | |
| EP | 1487535 B1 * | 6/2012 | ......... | A61B 5/02028 |
| EP | 1935448 A1 | 6/2020 | | |
| WO | 2003082080 A1 | 10/2003 | | |
| WO | 2008048471 A1 | 4/2008 | | |
| WO | 2014018092 A1 | 1/2014 | | |

OTHER PUBLICATIONS

International Search Report and Written Opinion received for PCT Serial No. PCT/GB2018/052076 on Oct. 1, 2018, 8 pgs.
International Preliminary on Patentability received for PCT Serial No. PCT/GB2018/052076 on Jun. 25, 2019, 17 pgs.

* cited by examiner

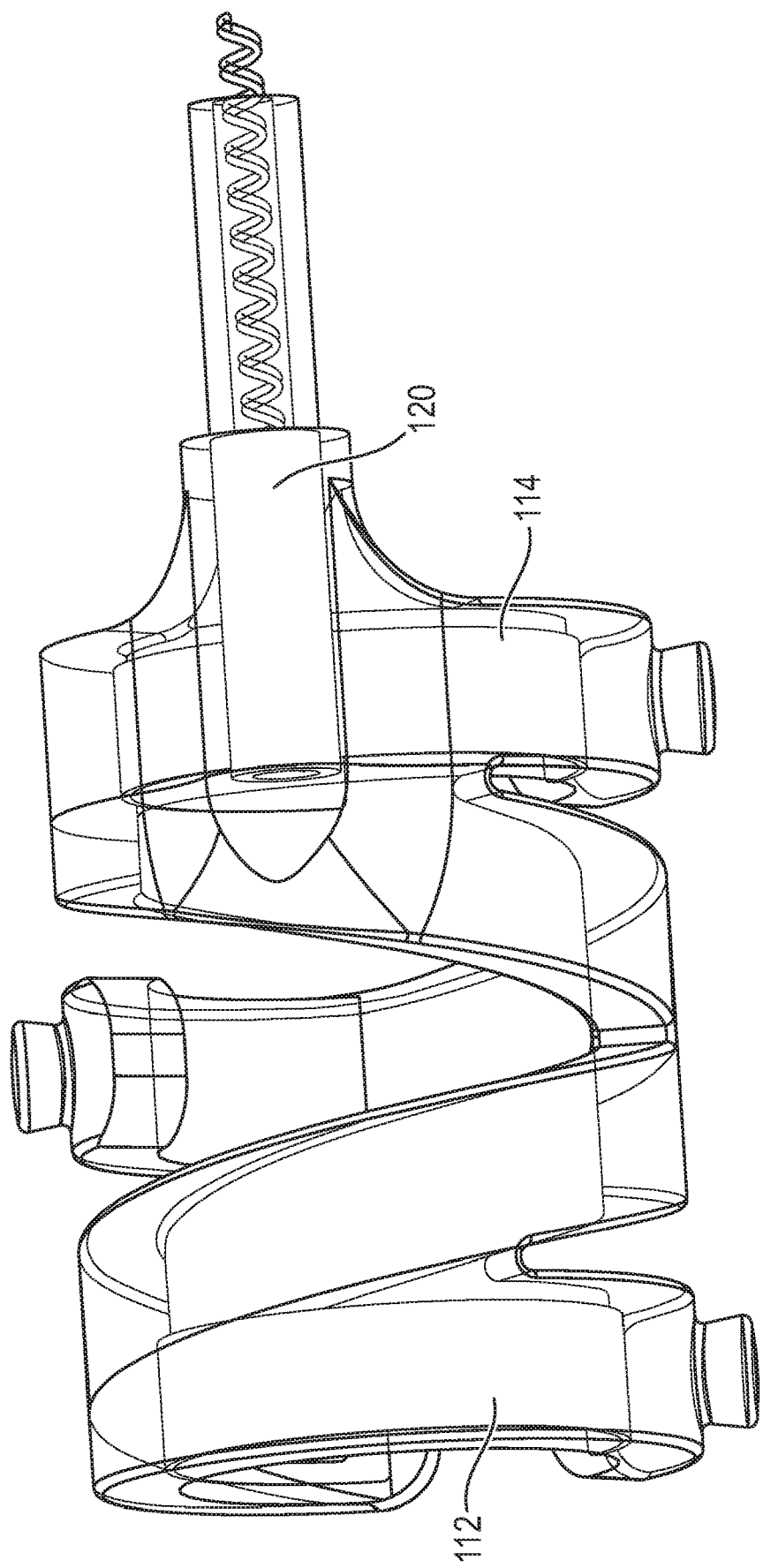

ELECTRODE DEVICES FOR NEUROSTIMULATION

PRIORITY CLAIM

The present application is a continuation of U.S. application Ser. No. 16/619,396, which is in turn a National Phase entry of PCT Application No. PCT/GB2018/052076, filed Jul. 23, 2018, which claims priority from U.S. Provisional Application No. 62/538,359, filed Jul. 28, 2017, and U.S. Provisional Application No. 62/608,386, filed Dec. 20, 2017, and U.S. Provisional Application No. 62/692,426, filed Jun. 29, 2018, each of which is hereby fully incorporated herein by reference.

BRIEF DESCRIPTION

The present disclosure is related to embodiments of extravascular and intravascular devices containing electrodes for neurostimulation of a vessel. The devices are housed in flexible substrates, each substrate having a spine through which conductors for the electrodes are routed and housed. Extending from the spine are a plurality of curvilinear flaps or arms that support the electrodes and position the electrodes to either be inward facing, i.e., extravascular designs, or outward facing, i.e., intravascular designs. The substrate flaps or arms may include one or more electrodes and be configured to place one or more of the electrodes at specific positions relative to the target vessel.

BACKGROUND

Electrical devices of various shapes and sizes including one or more electrodes have been used for neurostimulation of target anatomy for years. U.S. Pat. No. 8,755,907 discloses an extravascular device including one or more electrode ribs interconnected by a spine, and optionally including one or more non-electrode ribs that serve to isolate the electrode ribs from movement and forces transmitted by cables near the non-electrode ribs. Both types of ribs are sized to fit the target anatomy and are positioned around the target vessel by separating the ribs, placing them around the target vessel, and closing them to secure them about the target vessel. The ends of the ribs may then be sutured in place, or not, but if not sutured the ends of ribs may be formed of a stiff material, including metal, provided it is electrically isolated from the electrodes.

U.S. Pat. Pub. No. 2016/0296747 discloses an intravascular neurostimulation device that may be collapsed so that it can be inserted into a catheter for positioning within a target vessel. Once in position, the distal end of the device is uncovered from the catheter, either by pushing the distal end of the device from the distal end of the catheter or removal of the catheter once the distal end of the device is in place. As disclosed, the device has a plurality of elongated balloon arms that have a number of electrodes positioned along the outer surface of each of the elongated balloon arms. As the device leaves the catheter, the device expands (i.e., balloons) so that the outer surface of each of the elongated balloon arms moves into contact with the interior walls of the target vessel in which it is placed. Other devices use a metal cage, typically formed of nitinol, with electrodes placed around the exterior surface of the cage, which are naturally biased to an expanded position, but can be compressed to fit within the catheter.

U.S. Pat. No. 9,283,379 discloses a cuff electrode assembly with a resilient body configured to be disposed about a target vessel. The cuff body includes a first end portion having a first free end, and a second end portion having a second free end. The cuff electrode assembly further includes a first arm member and a second arm member each projecting radially outward from the cuff body and spaced from one another along the cuff body. Application of a force pushing the first and second arm members toward one another defines an opening of the cuff body that allows the cuff body to be positioned around the target vessel.

U.S. Pat. No. 8,855,767 discloses an electrode cuff that includes a polymer cuff body having a pocket or pouch into which a target vessel can be positioned such that the electrodes of the cuff are proximate the nerve.

U.S. Pat. No. 7,925,352 discloses a cage-like electrode device with an array of electrodes disposed along a flexible elongated member that is configured to be positioned in contact with a target vessel wall. Pairs of rib-like structures, positioned at each electrode, contact the interior of the vessel walls to position the device. U.S. Pat. No. 9,216,280 discloses an electrode device that includes an elongated shaft and pairs of extending curvilinear arms or ribs extending from opposing sides of the elongated shaft. Each of the arms or ribs includes electrodes that make contact with the interior target vessel walls.

Each of the above examples illustrate a variety of existing different cuff-like and cage-like designs, with arms or flaps that are either perpendicular to the length of the target vessel, horizontal to the length of the target vessel, fit substantially fully around the target vessel and include exterior portions that can be used to open the cuff for placement and removal, or are more rigid in nature and cover only a portion of the target vessel. Such conventional designs lack radial flexibility and self-sizing capabilities. If the target vessel is excessively compressed by the device, nerve damage may result from the decreased blood flow and constricted nerve fibers. Temporary swelling of the target vessel caused by the trauma of the positioning of the device can exacerbate such nerve damage. In contrast, loose fitting devices can result in poor electrical contact and low treatment efficiency, which can further degrade over times as a result of ingrowth of connective tissue between the target vessel and the device.

Conventional helical or serpentine electrode devices address some of the limitations of conventional rigid cuff-like and cage-like devices, such as permitting some radial expansion that helps with post-positioning edema or swelling of the target vessel, more fluid exchange with surrounding tissue, better electrical contact, and reduced growth of connective tissue. Helical or serpentine devices, however, require a complex positioning effort that requires significant dissection and nerve manipulation in order to wind the helix around the nerve at least two times. Positioning of such devices also requires mobilization of a large portion of the nerve because the cathode and anode electrodes are typically positioned by their own device.

SUMMARY

According to one aspect of the present disclosure, there is a neural interface for interfacing with a target vessel, comprising: a first end portion, a second end portion and a center portion positioned between the first end portion and the second end portion, wherein the first end portion includes at least a first electrode and the second end portion includes at least a second electrode, wherein the first end portion, the second end portion and the center portion are each formed of a flexible material that is configured to enable each of the first end portion, the second end portion and the center portion to self-size to a surface of the target vessel when the neural interface is released at a position along the target vessel, and wherein neither the first end portion, the second end portion nor the center portion form a closed circumscribed circular arc around the target vessel at any point along a length of the target vessel; and a spinal portion configured to house electrical conductors for the first electrode and the second electrode, the spinal portion being connected to one or more of the first end portion, the center portion and the second end portion.

The first end portion, the second end portion and the center portion each have an initial configuration that is formed when these portions are in a rest state. The first end portion, the second end portion and the center portion are each biased towards the initial configuration, for instance when displaced from the initial position. In this way, it is possible for the first end, second end and center portions to self-size to the surface of the target vessel. This allows the neural interface to be positioned in a single pass around the nerve/vessel with minimal manipulation of the nerve/vessel and provides a reduction in tissue dissection around the area of the nerve/vessel where the interface is positioned.

The flexible material may be non-rigid and capable of elastic deformation (i.e. reversible deformation). In this way the first end portion, the second end portion and the center portion can each be displaced from their initial resting state into a different state in order to position the interface with respect to the target vessel. Then, when the interface is in an appropriate position the interface can be released allowing the portions to be urged back to their resting state, thus softly gripping the target vessel.

In the interface, none of the first end portion, the second end portion and the center portion forms a closed circumscribed circular arc around the target vessel at any point along a length of the target vessel. In other words, each one of the first end portion, the second end portion and the center portion form a gap when positioned around the target vessel. Thus, the target vessel can sit in alignment with the gaps formed by the portions, and therefore may serve to ensure that the target vessel may pulsate without constriction. In addition, the gaps provided by the portions allow an initially swollen target vessel to return to a normal state over time without constriction of the target vessel when it is swollen and without losing electrode to target vessel contact when the target vessel is in its normal state.

The spinal portion comprises an elongate member comprising a conduit for electrical conductors for the first electrode and the second electrode. In some examples, the spinal portion includes the electrical conductors. The spinal portion provides a simple and convenient arrangement for providing electrical connectivity to the first electrode and the second electrode.

The first end portion may be a positioned towards a first end of the neural interface and the second end portion may be positioned towards a second opposing end of the neural interface. The first end portion and second end portion may be positioned on opposite sides of the center portion. The first end portion, the second end portion and the center portion may be concentric with respect to one another.

The center portion may be referred to as an intermediate portion, since it is positioned between the end portions. The center portion may be positioned centrally with respect to the neural interface; however, the central/intermediate portion may be positioned at a location offset from the center of the neural interface. In addition, the center portion may be positioned equidistance from each end portion. Alternatively, the distance between the first end portion and the center portion may differ to the distance between the second end portion and the center portion.

The spinal portion may be an assembly made up of a plurality of parts. Each one of these parts may be connected, directly or indirectly, to one or more of the first end portion, the center portion and the second end portion.

In the present disclosure, a vessel refers to a vessel and a nerve (or nerves) that travels along with the vessel. The vessel may be an artery (or arteries) and/or a vein (or veins) and/or a lymph vessel (or lymph vessels). A nerve that travels along a vessel may be a nerve that is adjacent to the vessel or a nerve that is in the vicinity of the vessel.

In the present disclosure, a target vessel may be a target vessel that includes a nerve (or nerves) that travels along with the vessel. The target vessel may be an artery (or arteries), and/or a vein (or veins), and/or a lymph vessel (or lymph vessels).

BRIEF DESCRIPTION OF THE SEVERAL VIEWS OF THE DRAWING

FIG. 2A is a perspective view of an opposite side of the embodiment of FIG. 1;

DETAILED DESCRIPTION

The present disclosure is related to embodiments of extravascular and intravascular neural interface devices containing electrodes for neurostimulation of a target vessel. The devices may be housed in flexible substrates, each substrate having a central portion through which conductors for the electrodes are routed and housed. Extending from the central portion are a plurality of curvilinear flaps or arms that support the electrodes and position the electrodes to either be inward facing, i.e., extravascular designs, or outward facing, i.e., intravascular designs. An extravascular neural interface device is configured to be positioned outside of the target vessel, while an intravascular neural interface device is configured to be positioned at least partially within the target vessel. The substrate flaps or arms may include one or more electrodes and be configured to place one or more of the electrodes at specific positions relative to the target vessel.

Figure 1:
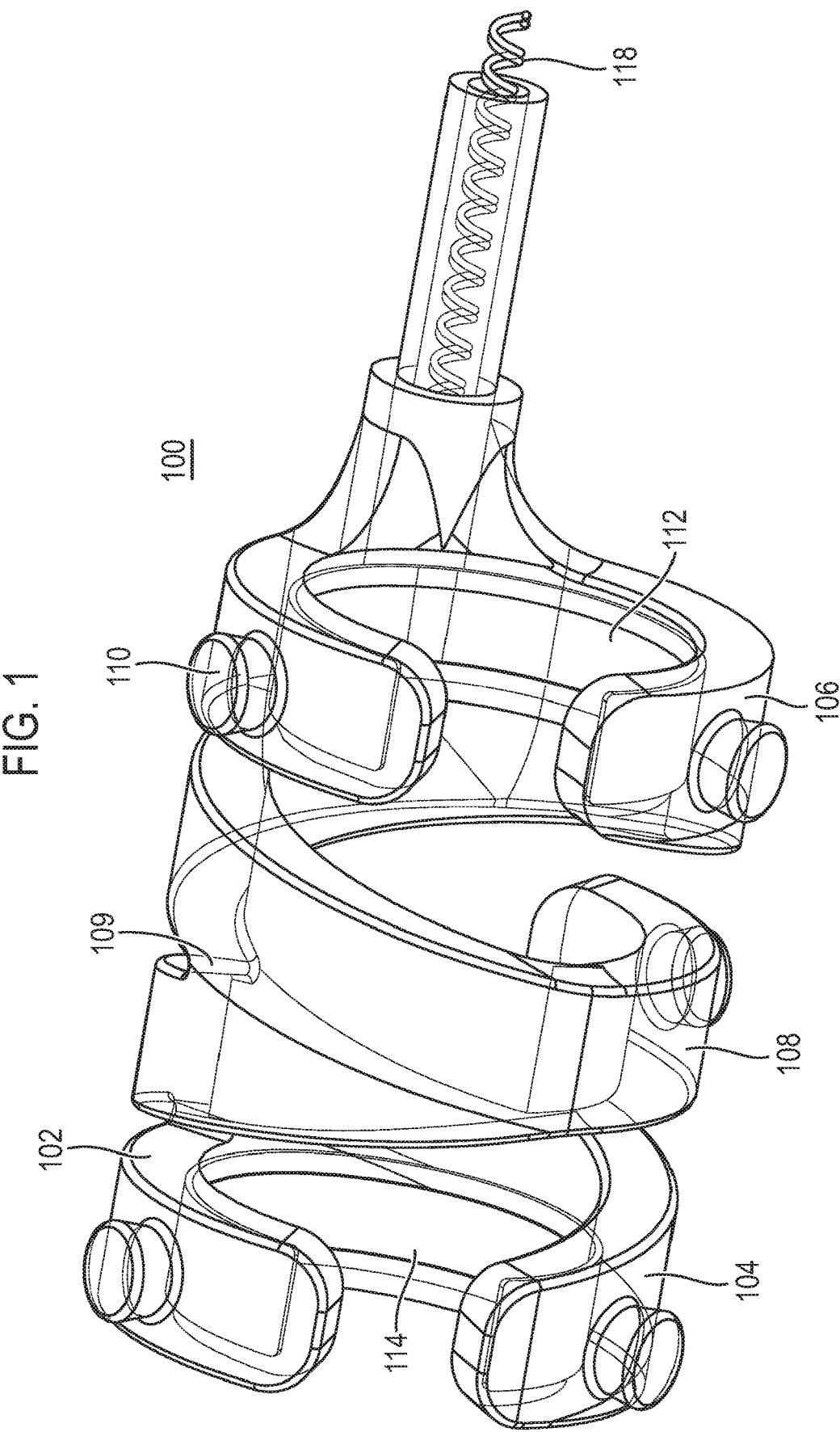
FIG. 1 is a perspective view of a first side of an embodiment of a bipolar electrode device including a flexible semi-helical structure for holding the electrodes and positioning the device.

An embodiment of a bi-polar, extravascular neural interface in accordance with the present disclosure is illustrated in FIGS. 1 and 2A. The neural interface 100 may comprise a hybrid cuff, including a partially-helically formed supporting substrate 102, manufactured of silicone or a similar flexible substance, such as styrene isoprene butadiene (SIBS), polyamide, parylene, liquid-crystal polymer (LCP), polytetrafluoroethylene (PTFE), polyethylene (PE), polypropylene (PP), fluorinated ethylene propylene (FEP), ethylene-tetrafluoroethylene (ETFE), polyurethane, or another biocompatible polymer, Biocompatible silicone and some other grades of silicone can be very flexible and soft, thereby minimizing mechanical mismatches between a cuff and a target vessel and minimizing constriction on the target vessel. Polymer materials may also be used, but those materials may be stiffer and harder than silicones and may require thinner material to be used, which may be both an advantage and a drawback.

The substrate 102 may include two C-ring portions 104 and 106, each connected by a spinal portion forming a helix of one turn (when combined with a center portion 109 and one of the portions 104 or 106) in the opposite direction from a common center section 108 of a central portion 109, and ending in an C-ring configuration where the C-ring is substantially orthogonal to the target vessel once positioned. Arranged within each C-ring end portion 104 and 106 may be multiple platinum or platinum alloy electrodes (or electrode arrays), such as electrode arrays 112 and 114, versus multiple helical structures as in conventional systems. The electrodes arrays 112 and 114 may be of a conventional type and wired to a controller through conventional conductors 118, such as 35N LT® DFT (Drawn Filled Tubing) with a 28% Ag core, in a stranded cable configuration (i.e., 7×7 configuration—not shown), or in a multi-filar coil configuration. The conductors are housed in a spine or spinal portion 120 that is affixed to end portion 106 and part of central portion 109.

The configuration of the neural interface 100 may make it possible to significantly shorten the length of the neural interface 100, thereby reducing the portion of target vessel or nerve that needs to be mobilized during placement. In addition, the opposing helical directions of the portions 104 and 106, which each have a low helix angle relative to the spinal portion 120 may allow the neural interface 100 to be deployed and wound around the target vessel in one pass instead of at least two, as with conventional helical structures. A low helix angle or low pitch may allow the length of the neural interface 100 (or its distal end) to be shorter, which may result in less dissection of tissue during positioning.

The substrate 102 may include a number of attributions 110 placed at different points on or in the substrate 102. The attribution may be configured to enable a deployment tool (not shown) to grip, manipulate and deploy the neural interface 100. Thus, each attribution may be referred to as a deployment feature. The attributions may be protrusions. One or more protrusions may include one or more openings or eyelets for receiving a stylet (made of tungsten or similar material), for instance, in order to enable portions of the substrate to be straightened and/or to deploy the neural interface. The attributions 110 may also be openings, eyelets or some other form of lumen that may be equally manipulated by a deployment tool.

In an embodiment, the attributions 110 may be placed sufficiently near the open ends of the C-rings of portions 104 and 106 and near the end of center section 108 to enable the deployment tool to grip the attributions and simultaneously open the portions 104 and 108 and the center section 108 so that the neural interface may be positioned around the target vessel (not shown). As referred to herein, "open ends" refer to the ends positioned around the circumference of the C-rings, which are not attached to another feature (e.g., another C-ring or a spinal portion). In other words, each one of the "open ends" forms a side of a gap for the target vessel. Similarly "closed ends" refer to ends positioned around the circumference of the C-rings which are attached to another feature. In other words, each one of the "closed ends" does not form a gap for the target vessel. Once the neural interface 100 has been positioned around the target vessel, the deployment tool would carefully release the attributions so that the portions 104 and 108 and the center section 108 may softly self-size to the target vessel. By "self-size" it is meant that the neural interface 100 conforms to the shape of the target vessel of its own accord.

Figure 2B:
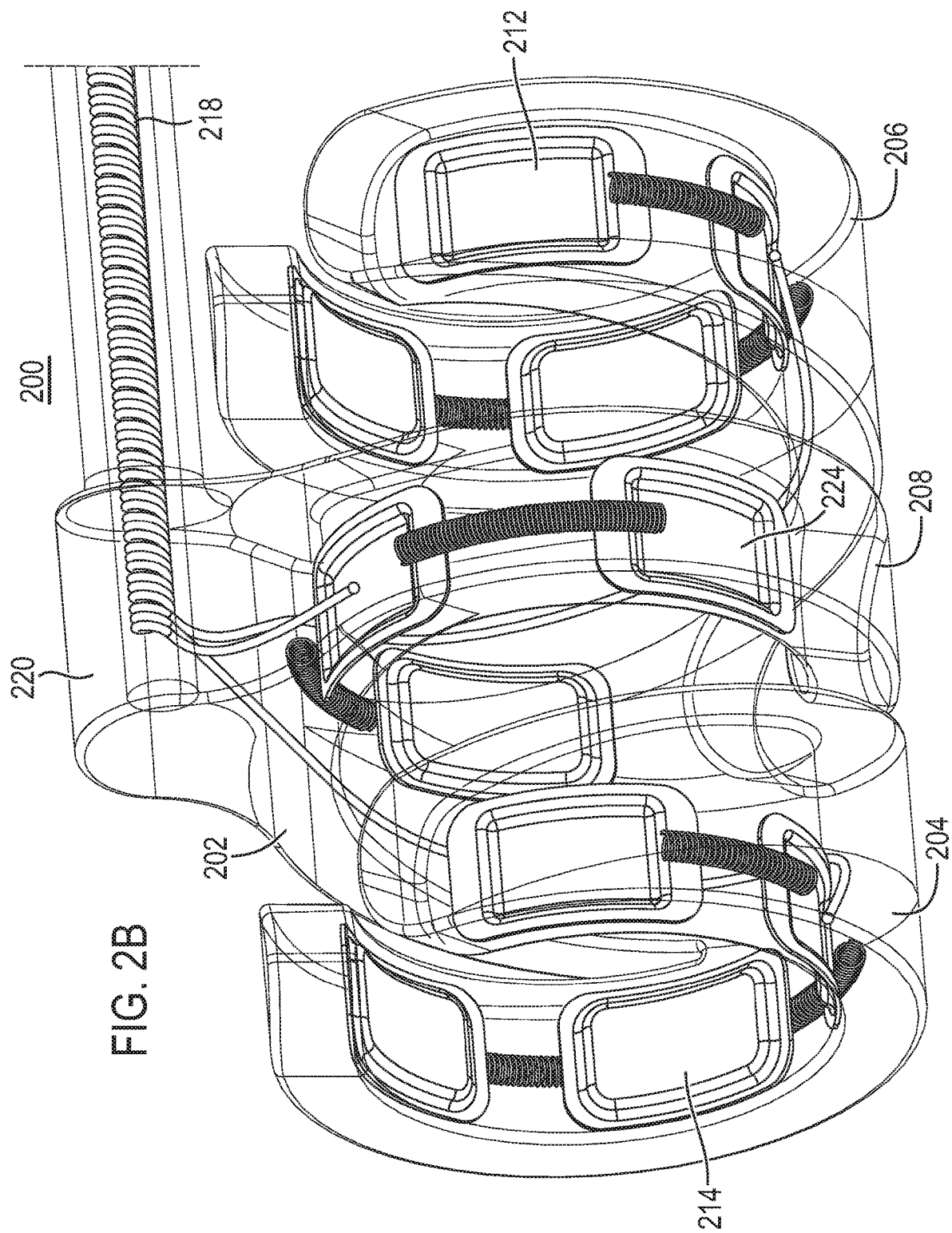
FIG. 2B is a perspective view of an embodiment of a multipolar electrode device including a flexible semi-helical structure similar to FIG. 1 and FIG. 2A

Another embodiment of a neural interface 200, similar in structure to the embodiment illustrated in FIGS. 1 and 2A, i.e., with multiple C-rings, a common center section, and forming two helical turns over a short length, is illustrated in FIG. 2B. Neural interface 200 may be multipolar instead of bipolar as may be the case with neural interface 100. In neural interface 200, the substrate 202 may include three C-ring portions 204, 206 and 208, with each C-ring end portion 204 and 206 connected by a one turn helix in the opposite direction from a common center section of an C-ring central portion 208, and ending in C-ring configurations that may be orthogonal to the target vessel once positioned on the target vessel. C-ring central portion 208 may also be orthogonal to the target vessel. Positioned within each C-ring portion 204, 206 and 208 may be multiple platinum or platinum alloy electrodes (or electrode arrays), such as electrode arrays 212, 214 and 224, fashioned (arranged) in such a way that electrodes in one C-ring covers the gap (along a length between electrodes) in the adjacent C-ring. Each electrode array is connected to a different conductor of the multi-conductor 218 housed in spinal portion 220, which is affixed to just central portion 208. The substrate 202 of neural interface 200 may not include attributions. Connecting individual electrodes or different arrays of electrodes to different conductors may enable selective stimulation of the target vessel by individually controlling each connected device.

Figure 3:
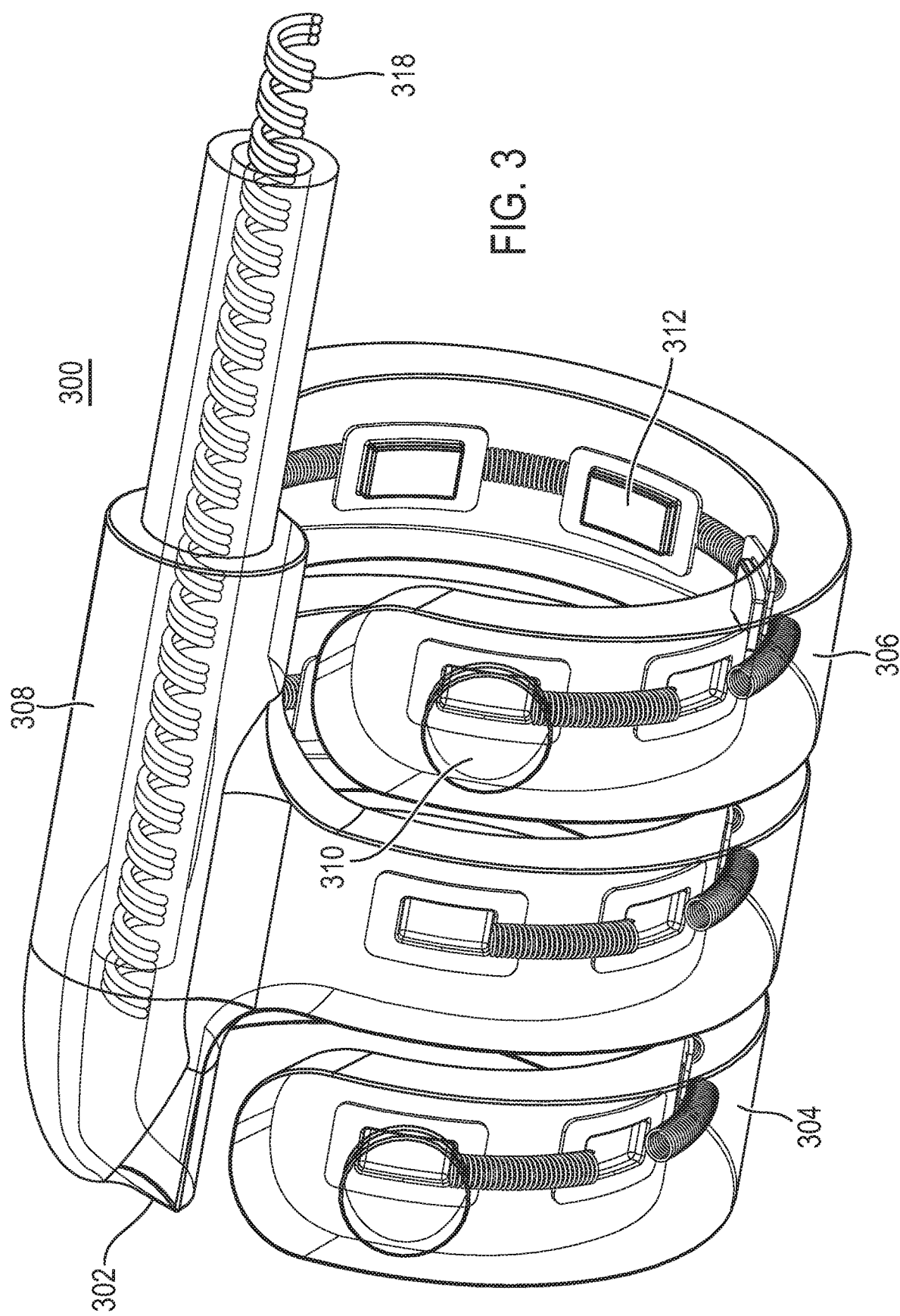
FIG. 3 is a perspective view of a first side of an embodiment of a tripolar electrode device including a flexible structure.
Figure 4A:
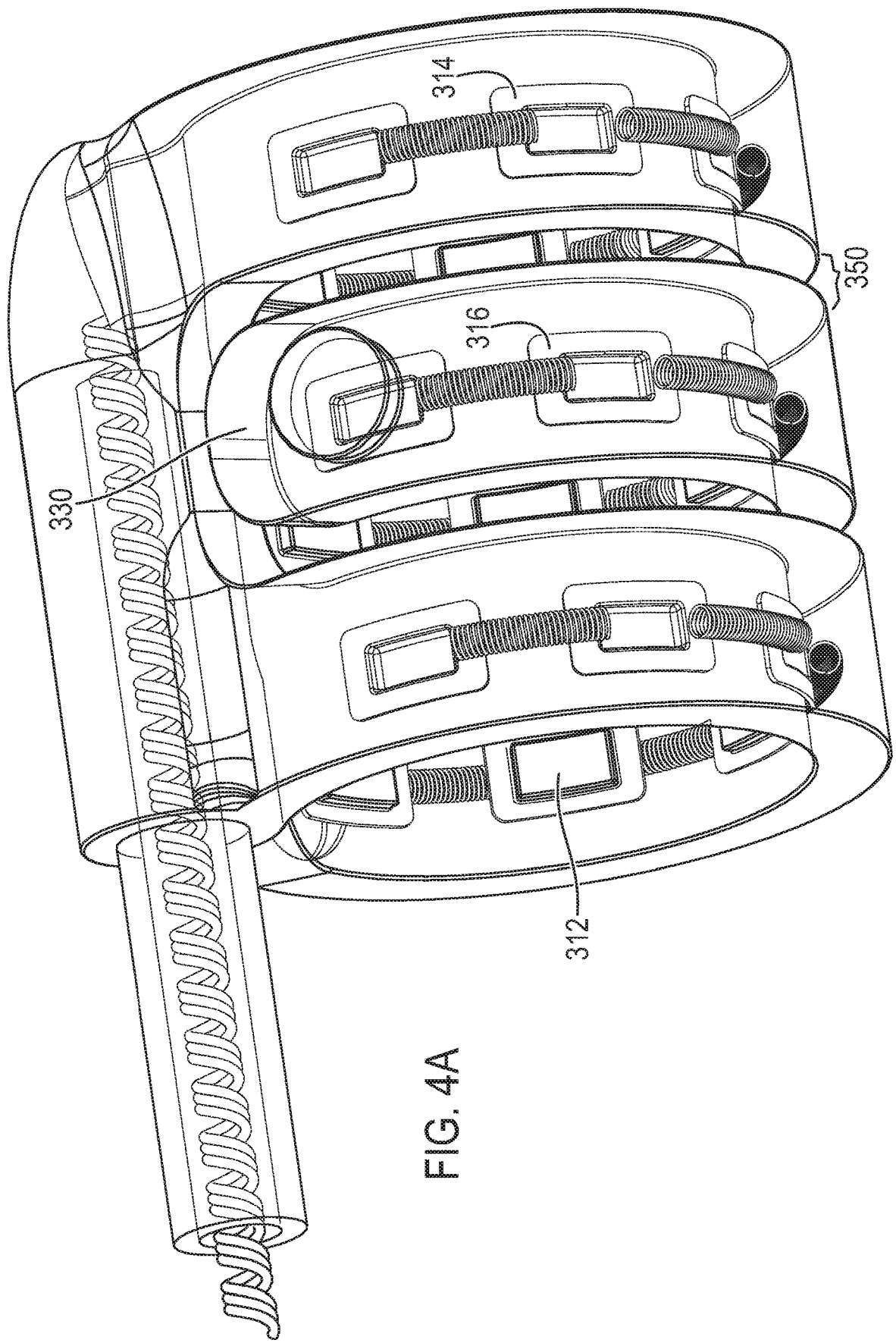
FIG. 4A is a perspective view of an opposite side of the embodiment of FIG. 3.

FIGS. 3 and 4A illustrate an embodiment of a tripolar neural interface 300 in accordance with the present disclosure. The neural interface 300 may be similar to neural interface 100 in that it may be formed of a flexible substrate 302 of similar material and may have two end portions 304 and 306 forming C-ring configurations that may be affixed to a spinal portion 308. However, unlike neural interface 100, the two end portions 304 and 306 may also not be connected to the center section. Instead, a center portion 330 forming a third C-ring may be utilized. The end portions 304 and 306 and the center portion 330 may have a very low helix angle, i.e., pitch, relative to the spinal portion 308, which enables the neural interface to be helical, but still have a significantly shorter length. The helix angle may be between approximately 15 and 30 degrees, but may also be less than 15 degrees.

As with neural interface 100, each of the C-rings of the neural interface 300 may include one or more electrodes or an array of electrodes, such as 312, 314 and 316, each connected to a conductor 318 through the spinal portion 308. A one electrode design may make it possible to maximize electrode coverage while minimizing the conductor interconnection process, such as through laser welding, resistance welding, etc. However, to minimize the rigidity of the electrode, i.e., making it sufficiently flexible, the electrode may have to be very thin (typically between 25 um and 50 um), which may make the interconnection of the conductors to the electrodes more challenging. Also, to keep the electrode as flexible as possible, surface features may not be possible to add to the electrode as it would decrease the electrode flexibility. For this reason, a one electrode may feature recessed electrodes with silicone rims or silicone webbing that may serve to hold the electrode in place. However, recessing the electrode may potentially decrease the efficacy of the stimulation. On the other hand, "segmented" electrode designs may provide better mechanical compliance, create the possibility of surface features, i.e., protruding electrodes, and make it possible to control each electrode individually (i.e., current steering). The trade-offs include limited electrode coverage, increased interconnection processes, decreased retention force. Segmented electrodes provide increased flexibility to the neural interface, thereby making it possible open a C-ring with a deployment tool wider and for a longer period of time, without creating excessive stress on the electrodes, than might be possible with a single electrode.

As shown in FIGS. 2A and 4A, the individual electrodes of the electrode arrays 112 and 114 of neural interface 100 and electrode arrays 312, 314 and 316 of neural interface 300 may be evenly spaced within the substrates 102 and 302, respectively. By evenly spacing the electrodes within the substrates, the inter-electrode distance is more constant, which may provide a more uniform current density distribution and enhancement of the effectiveness of the neural interfaces. In some embodiments, the position of the electrodes in the arrays may be staggered in order to achieve better electrical coverage. Certain characteristics of the neural interfaces 100 and/or 300, such as, with respect to neural interface 300, the spacing 350 between the electrode arrays 312, 314 and 316, the size and shape of the electrodes, the size and shape and number of electrodes in electrode arrays, the inter-electrode distance within electrode arrays, and the angle of the helix angle, may each be chosen for the particular application of the neural interface. For example, utilization of the neural interface for treatment of the splenic artery may require different characteristics than utilization of the neural interface for treatment of a different vessel. For instance, when utilized for splenic artery treatment an electrode width of approximately 1-4 mm, with preferred width ranges of between approximately 1-2 mm and approximately 2-3 mm, may be appropriate. When utilized for treatment of different vessels, different electrode widths may be desirable.

The neural interface 300 may also include at least one attribution 310 that may be positioned on the outer surface of the substrate 302 near the open ends of each C-ring of the portions 304, 306 and 330. As noted above, the attributions may include one or more openings or eyelets for receiving a stylet (made of tungsten or similar material), for instance, in order to enable portions of the substrate to be straightened and/or to deploy the neural interface. The attributions 310 may be configured to enable a deployment tool (not shown) to grip, manipulate and deploy the neural interface 300. In an embodiment, the attributions 310 may be placed sufficiently near the open ends of the C-rings of portions 304, 306 and 330 to enable the deployment tool to grip the attributions 310 and simultaneously open the portions 304, 308 and 330 so that the neural interface 300 may be positioned around the target vessel (not shown). Once the neural interface 300 has been positioned around the target vessel, the deployment tool would carefully release the attributions so that the portions 304, 308 and 330 may softly self-size to the target vessel. The configuration of the neural interfaces 100 and 300 may enable the neural interfaces to be positioned in a single pass around the nerve/vessel with minimal manipulation of the nerve/vessel and a reduction in tissue dissection around the area of the nerve/vessel where the interface is positioned.

Figure 4B:
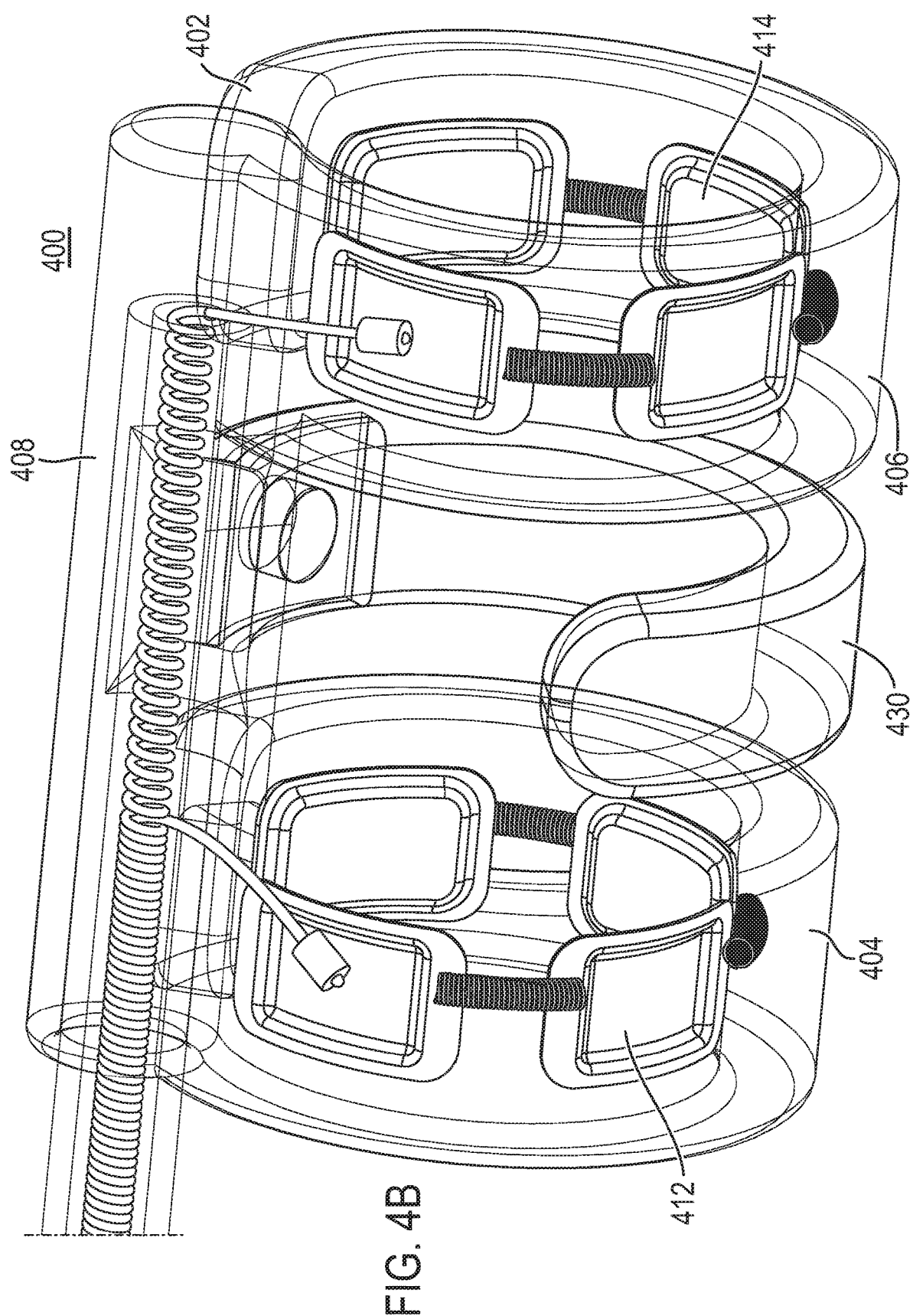
FIG. 4B is a perspective view of an embodiment of a bipolar electrode device including a flexible structure similar to FIG. 3 and FIG. 4A.

The neural interface 400 in FIG. 4B is similar to the neural interface 300. Neural interface 400 is formed of a flexible substrate 402 of similar material and may have two end portions 404 and 406 forming C-ring configurations containing electrode arrays 412 and 414. A center portion 430 may be affixed to a spinal portion 408 along with end portions 404 and 406. The center portion 430 may not include any electrodes, serving just to retain the neural interface once positioned, but embodiments may include electrodes.

The neural interfaces 100, 200, 300 and 400 may be self-sizing; meaning that they may be formed of flexible materials that allow them to be manipulated for deployment, but when released return to a predetermined shape, much like a nitinol cage can be reduced down to fit in a catheter and return to its pre-reduced shape once released from the catheter. This may enable the neural interfaces to be used to accommodate anatomical variability of the intervention site, yet still provide good electrical contact between the electrode arrays and the surface of the nerve/vessel, thereby improving the efficient of the interface. The flexible material of the interface may remain compliant even when it has self-sized to a nerve or vessel. This may help to prevent the neural interface from compressing a nerve or vessel and causing reduced blood flow and otherwise constricting nerve fiber. This may also better accommodate radial expansion of the nerve/vessel as a result of post-positioning edema or swelling and may accommodate the pulsatile behavior of intervention sites such as arteries.

The naturally open structure of the helix of the neural interfaces 100, 200, 300 and 400 may reduce coverage of the nerve/vessel periphery to promote more normal fluid and nutrient exchange with the intervention site and surrounding tissue. This may also help to minimize growth of connective tissue between the electrode nerve/vessel interfaces. The open structure of each neural interface is configured such that no end portion or center portion forms a closed circumscribed circular arc around the target vessel at any point along a length of the target vessel. In other words, no closed circle covering 360 degrees of an orthogonal portion of the target vessel's length is formed by the structure. This open unrestricted trench may serve to ensure that the target vessel may pulsate without constriction and that an initially swollen target vessel can return to a normal state over time without constriction of the target vessel when it is swollen and without losing electrode to target vessel contact when the target vessel is in its normal state.

Figure 5:
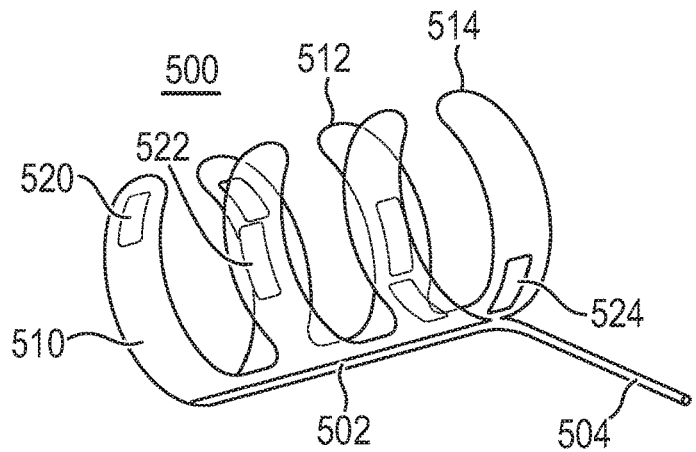
FIG. 5 is a perspective view of an embodiment of an extravascular Venus FlyTrap electrode device.
Figure 6:
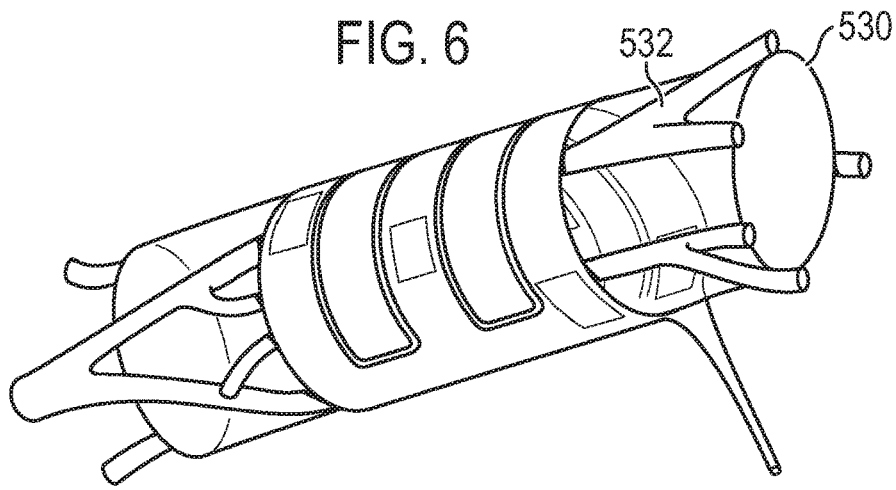
FIG. 6 is a perspective view of an embodiment of an extravascular Venus FlyTrap electrode device.

FIGS. 5 and 6 illustrate an additional embodiment of a self-sizing extravascular neural interface 500. The neural interface 500 may be shaped more like a Venus FlyTrap clasp, with a spinal portion 502 connected to a conduit 504 including conductors for the neural interface, and sets of matching portions 510, 512 and 514 extending from the spine 502. The portions 510, 512 and 514 may be substantially orthogonal to the spinal portion 502. Each of the end portions 510 and 512 and the center portion 514 may include an electrode or electrode array 520, 522 and 524, respectively, facing inward so that there may be a good electrical contact between the electrodes and the exterior walls of the target vessel/nerve 530, and allow the artery to pulsate more freely. As previously discussed, this open trench may relieve pressure on the nerves 532 in the target vessel 530 that are sandwiched between the arterial wall and the neural interface 500. The spacing or channels between the portions 510, 512 and 514 may also provide space for the target vessel to pulse and for fluids and nutrients to get to the target vessel.

The electrode or electrode arrays 520, 522 and 524 may also be positioned at different locations within each of the portions 510, 512 and 514. The number of electrodes and their placement with the electrode arrays may vary. As shown in FIGS. 5 and 6, electrode 520 of end portion 510 is positioned near the tip of the end portion 510, electrode 522 of center portion 512 is positioned near the middle of the center portion 512, and electrode 514 of end portion 514 is positioned near the connection point of the end portion 514 to the spinal portion 502. Naturally, different positional configurations (i.e., all electrodes at the tips, middle or spine of the portions, or any other combination of positions) may be possible and particularly selected to provide different circumferential coverage for the type of nerve/vessel and the treatment to be implemented.

As with the neural interface 100 and 300 described above, neural interface 500 is also self-sizing, in that the shapes of the portions 510, 512 and 514 are designed to substantially fit around most of the exterior circumference of the target vessel and the ribs are biased to a relaxed position that will cause them to wrap around most of the target vessel on their own accord once deployed. As used herein, the word "substantially" does not exclude "completely" e.g., a composition which is "substantially free" from Y may be completely free from Y. Where necessary, the word "substantially" may be omitted from the definition of the disclosure. For example, a substantially full turn of a helix may be a full turn of a helix, features positioned substantially opposite may be placed opposite, features spaced a substantially constant distance apart may be spaced a constant distance apart, and electrodes providing a substantially uniform current density may provide a uniform current density.

The portions 510, 512 and 514 may be orthogonal to the spinal portion 502 or at a low helix angel relative the spinal portion 502. The composition of the substrate for the neural interface 500, like neural interfaces 100 and 300, can be silicon or a similar material, and all such neural interfaces can be further treated to prevent early scar formation (i.e., fibrous tissue). Such treatment may be done only on selected surfaces, e.g., the side facing the nerve/arterial wall. For example, silicon may be doped with a steroid drug, such as dexamethasone. The outer surface of the substrate of the neural interface may also, or alternatively, be coated with a hydrophilic polymer, such as poly-2-hydroeyethyl-methacrylate (pHEMA).

The tips of each portion 510, 512, and 514 may be shaped to enable the portions to be griped by a deployment tool (not shown) for each placement on or removal from a target vessel and/or nerve. Alternatively, attributions, such as attributions 110 and 310 may be added to the exterior surface of the portions 510, 512 and 514 to enable the portions to be pulled back for placement on or removal from a target vessel and released when the neural interface 500.

Figure 7:
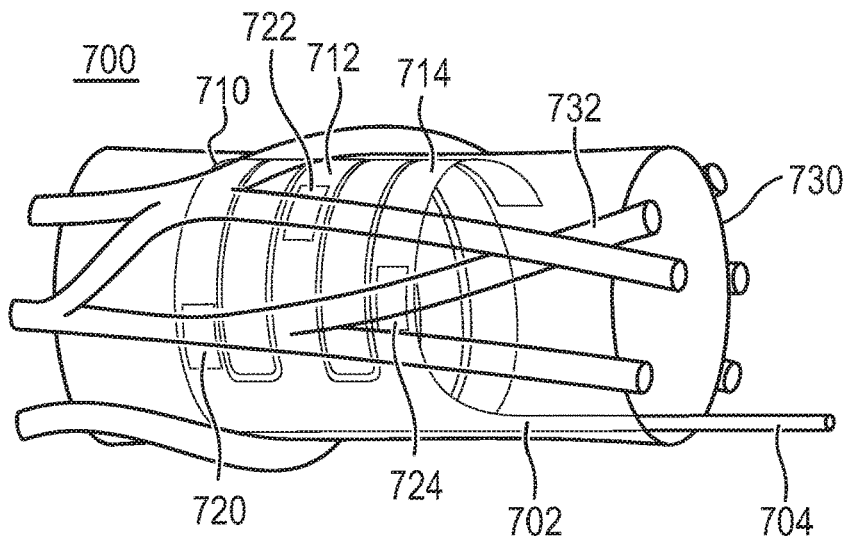
FIG. 7 is a perspective view of an embodiment of an intravascular Venus FlyTrap electrode device.

FIG. 7 illustrates an embodiment of a self-sizing intravascular neural interface 700. As with neural interface 500, neural interface 700 may be shaped like a Venus FlyTrap clasp, with a spinal portion 702 connected to a conduit 704 including conductors for the neural interface, and sets of matching portions 710, 712 and 714 extending from the spinal portion 702. However, in contrast to neural interface 500, each of the portions 710, 712 and 714 may include an electrode or electrode array 720, 722 and 724, respectively, facing outward so that there may be a good electrical contact between the electrodes and the interior walls of the target vessel/nerve 730, and allow the artery to pulsate more freely, which may relieve pressure on the nerves 732 in the target vessel 730 that are sandwiched between the interior arterial wall and the neural interface 700. The spacing or channels (low-pressure trench) between the portions 710, 712 and 714 may also provide space for the target vessel to pulse and unrestricted conduit for fluids and nutrients to get to the interior walls of the target vessel 730, while at the same time, not fully encircling the artery at any point of the cuff geometry. For example, with respect to each embodiment disclosed herein, no portion of the cuff geometry covers a circumference (a complete 360 degree rotation) of a portion of the target vessel orthogonal to any point on the spinal portion.

The electrode or electrode arrays 720, 722 and 724 may also be positioned at different locations within each of the portions 710, 712 and 714. As shown in FIG. 7, electrode 720 of end portion 710 is positioned near the connection point between the spinal portion 702 and the end portion 710, electrode 722 of center portion 712 is positioned near the middle of the center portion 712, and electrode 714 of end portion 714 is also positioned near the spinal portion 702. Naturally, different positional configurations (i.e., all at the tips, middle or spine, or any other combination of positions) may be possible and particularly selected for the range of the circumferential coverage of the nerve/vessel, for the type of nerve/vessel, and for the treatment to be implemented.

In contrast to the extravascular neural interfaces embodiments described above, neural interface 700 may be positioned via a flexible/collapsible catheter (with the neural interface 700 collapsed inside the catheter, not shown) versus an external deployment tools. Depending on the location of the target vessel, the positioning procedure may be minimally invasive. For example, for positioning in a splenic artery, the procedure may be performed through a total percutaneous access via standard (e.g., femoral) artery access. Once the catheter is positioned for deployment of the neural interface 700, the catheter may be withdrawn and the released neural interface will self-size to the inside of the target vessel 730, which requires the portions 710, 712 and 714 to be formed so their normal relaxed position will cause them to fold away from the spine 702 so as to make good contact with the interior walls of the target vessel 730.

Figure 8A:
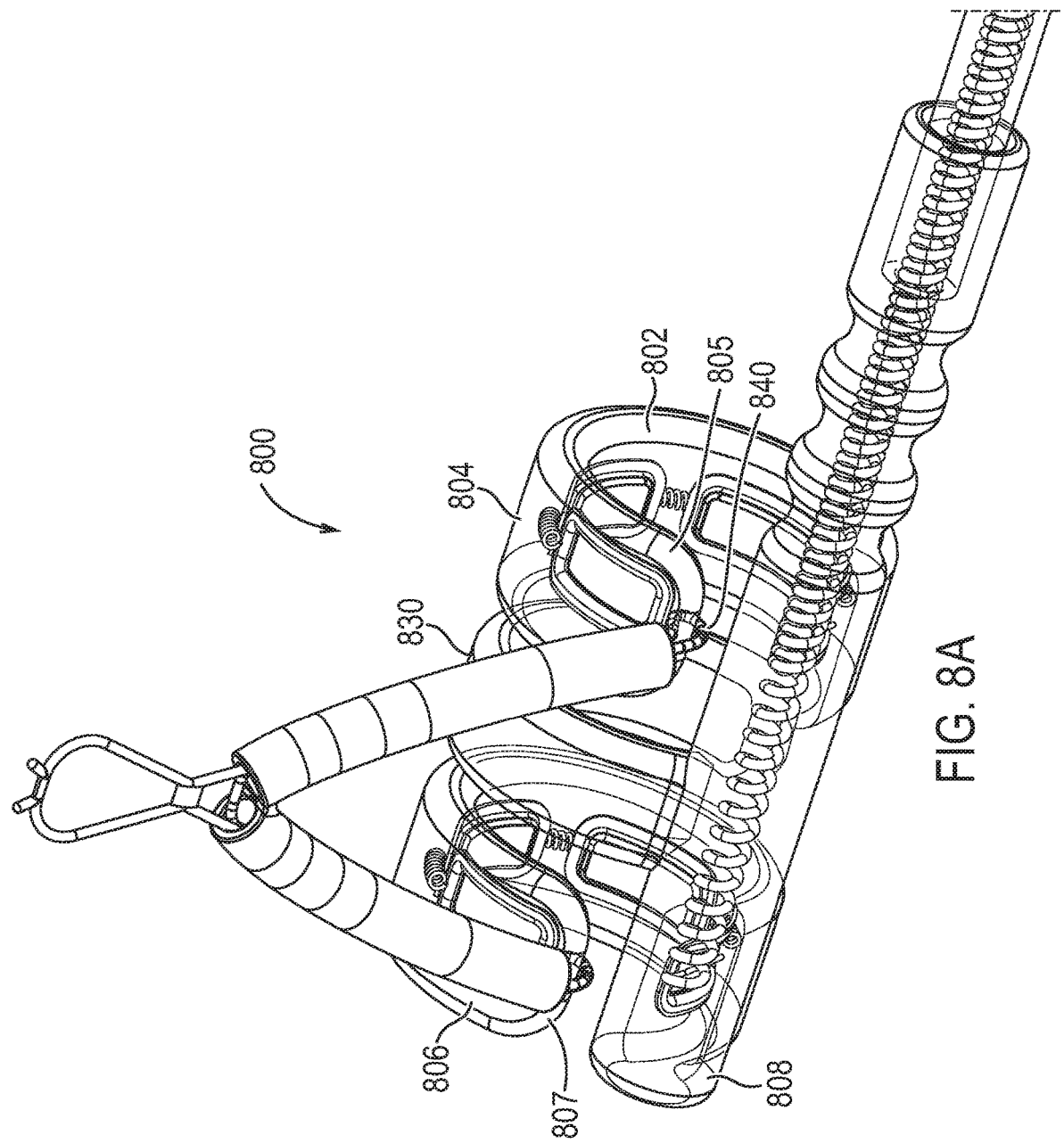
FIG. 8A is a perspective view of an embodiment of an extravascular bipolar electrode device including a flexible structure similar to FIG. 4B.
Figure 8B:
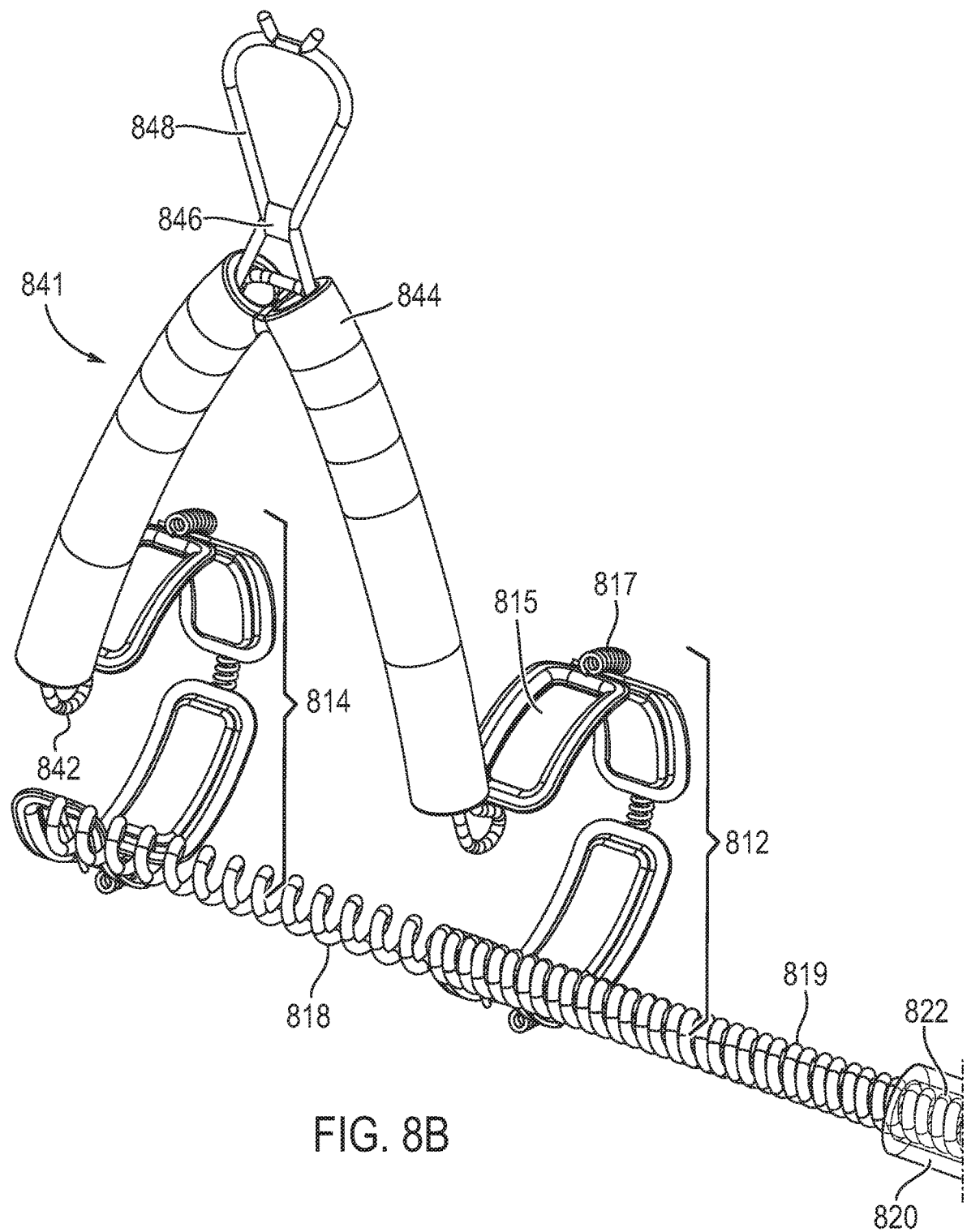
FIG. 8B is a perspective view of components of the embodiment of FIG. 8A.

In the embodiment of FIG. 8A, an extravascular bipolar electrode neural interface 800 is illustrated. The interface 800 includes a flexible structure similar to that of FIG. 4B. In FIG. 8B, the neural interface 800 of FIG. 8A is also depicted, but without a flexible substrate 802 and covering for the spinal portion 808, which serves to further illustrate internal components of the neural interface 800 and a deployment tool. The neural interface 800 is similar to the neural interface 400 in FIG. 4B. The flexible substrate 802 may be formed of material similar to that disclosed for neural interface 400. The neural interface 800 may include two arms at either end of the device, such as end portions 804 and 806, which may have open ends 805 and 807, respectively. The end portions 804 and 806 may each be in a C-ring configuration and contain electrode arrays, such as arrays 812 and 814 of FIG. 8B. A center arm portion 830 may be affixed to a spinal portion 808, as are the closed ends of end portions 804 and 806. The center portion 830 may not include any electrodes, serving just to retain the neural interface once positioned, but embodiments may include electrodes.

As shown in FIG. 8B, the four electrodes 815 of each array 812 and 814 are connected in series via three microcoil interconnects 817, which are in turn serially connected to a conductor 818, for array 814, and conductor 819, for array 812. The conductors 818 and 819 may be covered with the same flexible substrate material used to cover the end portions 804 and 806 and central portion 830 over the length of the spinal portion 808 and extending for a short distance from the neural interface 800, Before the conductors 818 and 819 exit the material of the spinal portion they are also covered with a silicon lead body tubing 820 to form the lead body conductor 822.

As previously noted, attributions may be protrusions, but may also be openings or eyelets. As illustrated in FIG. 8A, the attributions may be openings 840 formed at the open end 805 and 807 of end portions 804 and 806. The deployment tool 841 may be comprised of suture wire 842, grab tab tubing 844, a connector 846 and a grab tube loop 848. The suture wire 842 may be looped through each opening 840 and through the silicon tubing of grab tab 844. The suture wire 842 may then be brought together at connector 846 to form a grab tube loop 848. During deployment of the neural interface 800, a surgeon may position the central portion 830 around a target vessel (not shown in FIGS. 8A and 8B), while pulling lightly on the grab tube loop 848. Such pressure will pull the open ends 805 and 807 of end portions 804 and 806 away from the spinal portion 808 and make it possible to position the neural interface 800.

When the neural interface 800 is properly positioned, the pressure may be removed from the grab tube loop 848 so that the open ends 805 and 807 may softly self-size around the target vessel. Although not shown in FIGS. 8A and 8B, the central portion 830 may also include an opening attribution 840 so it may be opened in a similar manner to end portions 804 and 806 for self-sizing around the target vessel. Once the neural interface has been properly positioned, the suture wire 842 may be cut and removed from the openings 840. The opening attributions 840 may be circular holes, oval-shaped slots (not shown in FIGS. 8A and 8B) or other shapes, or eyelets (not shown in FIGS. 8A and 8B) that extend on tabs from the end portions 805 and 807.

The following is a non-exhaustive list of embodiments that may or may not be claimed:

1. A neural interface, comprising:
a first end portion, a second end portion and a center portion positioned between the first end portion and the second end portion, wherein the first end portion includes at least a first electrode and the second end portion includes at least a second electrode, wherein the first end portion, the second end portion and the center portion are formed of a flexible material that is configured to enable each of the first end portion, the second end portion and the center portion to self-size to a surface of a target vessel when the neural interface is released at a position along the target vessel, and wherein neither the first end portion, the second end portion nor the center portion form a closed circumscribed circular arc around the target vessel at any point along a length of the target vessel; and
a spinal portion configured to house electrical conductors for the first electrode and the second electrode, the spinal portion being connected to one or more of the first end portion, the center portion and the second end portion.

2. The neural interface of embodiment 1, wherein the first electrode is positioned toward a surface of the first end portion adjacent to an exterior surface of the target vessel, wherein the second electrode is positioned toward a surface of the second end portion adjacent to the exterior surface of the target vessel, and wherein the neural interface is extravascular.

3. The neural interface of embodiment 2, wherein the first end portion, the second end portion and the center portion each a semi-circular arc around the target vessel with at least one open end, wherein the first end portion, the second end portion and the center portion each include a deployment lumen positioned near the one open end, wherein each deployment lumen is configured to be griped by a deployment tool and pulled back to open each semi-circular arc and enable the first end portion, the second end portion and the center portion to be placed on the target vessel, and wherein the flexible material is biased to enable the first end portion, the second end portion and the center portion to self-size to fit around the target vessel when the deployment tool releases each deployment lumen.

4. The neural interface of embodiment 2, wherein the first end portion and the second end portion each form a semi-circular arc around the target vqessel with two open ends, wherein the center portion forms a semi-circular arc around the target vessel with one open end, a first closed end and a second closed end, wherein the first closed end is attached to the first end portion at a first point and the second closed end is attached to the second end portion at a second point, wherein a first section of the center portion between the first point and the open end forms a substantially full turn of a first helix, and wherein a second section of the center portion between the second point and the open end forms a substantially full turn of a second helix.

5. The neural interface of embodiment 4, wherein the first end portion and the second end portion each include a deployment lumen positioned near the open ends and the center portion includes a deployment lumen positioned near the one open end, wherein each deployment lumen is configured to be griped by a deployment tool and pulled back to open each semi-circular arc and enable the first end portion, the second end portion and the center portion to be placed on the target vessel, and wherein the flexible material is biased to enable the first end portion, the second end portion and the center portion to self-size to fit around the target vessel when the deployment tool releases each deployment lumen.

6. The neural interface of embodiment 2, wherein the first end portion, the second end portion and the center portion each form a semi-circular arc around the target vessel with one open end and one closed end, wherein each of the one closed end is attached to the spinal portion, wherein the center portion includes at least a third electrode attached to an electrical conductor housed by the spinal portion, and wherein the third electrode is positioned toward an interior surface of the center portion.

7. The neural interface of embodiment 6, wherein the first end portion, the second end portion and the center portion each include a deployment lumen positioned near the open end, wherein each deployment lumen is configured to be griped by a deployment tool and pulled back to open each semi-circular arc and enable the first end portion, the second end portion and the center portion to be placed on the target vessel, and wherein the flexible material is biased to enable the first end portion, the second end portion and the center portion to self-size around the target vessel when the deployment tool releases each deployment lumen.

8. The neural interface of embodiment 1, wherein the first end portion, the second end portion and the center portion are formed from two substantially opposing semi-circular arcs, wherein each semi-circular arc includes a closed end attached to the spinal portion and an open end, wherein an opening is formed between the open end of each semi-circular arc substantially opposite the spinal portion, wherein the center portion includes at least a third electrode attached to an electrical conductor housed by the spinal portion, wherein the third electrode is positioned toward an interior surface of the center portion.

9. The neural interface of embodiment 8, wherein each open end of each semi-circular arc is configured to be griped by a deployment tool and pulled back to further open each semi-circular arc and enable the first end portion, the second end portion and the center portion to be placed on the target vessel, and wherein the flexible material is biased to enable the first end portion, the second end portion and the center portion to self-size to fit around the target vessel when the deployment tool releases each open end.

10. The neural interface of embodiment 8, wherein each semi-circular arc includes at least one electrodesax positioned substantially opposite the at least one electrode of an opposing semi-circular arc thereby forming a pair of electrodes.

11. The neural interface of embodiment 10, wherein each pair of electrodes is positioned near the open end of each semi-circular arc, near the closed end of each semi-circular arc, or in-between the open end and the closed end of each semi-circular arc.

12. The neural interface of embodiment 1, wherein the first electrode is positioned toward an exterior surface of the first end portion, wherein the second electrode is positioned toward an exterior surface of the second end portion, wherein the neural interface is intravascular, wherein the first end portion, the second end portion and the center portion are formed from two substantial opposing semi-circular arcs, wherein each semi-circular arc includes a closed end attached to the spinal portion and an open end, wherein an opening is formed between the open end of each semi-circular arc substantially opposite the spinal portion, wherein the center portion includes at least a third electrode attached to an electrical conductor housed by the spinal portion, wherein the third electrode is positioned toward an exterior surface of the center portion.

13. The neural interface of embodiment 12, wherein the first end portion, the second end portion and the center portion are configurable to be placed inside a catheter for positioning within the target vessel, and wherein the flexible material is biased to enable the first end portion, the second end portion and the center portion to self-size to fit against interior walls of the target vessel when released from the catheter.

14. The neural interface of embodiment 12, wherein each semi-circular arc includes at least one electrode positioned substantially opposite the at least one electrode of an opposing semi-circular arc thereby forming a pair of electrodes.

15. The neural interface of embodiment 14, wherein each pair of electrodes is positioned near the open end of each semi-circular arc, near the closed end of each semi-circular arc, or in-between the open end and the closed end of each semi-circular arc.

16. The neural interface of embodiment 1, wherein the first electrode and the second electrode are electrode arrays including a plurality of inter-electrodes, wherein each inter-electrode is spaced a substantially constant distance from an adjacent inter-electrode to provide a substantially uniform current density.

17. The neural interface of embodiment 1, wherein the material is a silicon-based material.

18. The neural interface of embodiment 17, wherein the silicon-based material is doped with a steroid drug.

19. The neural interface of embodiment 17, wherein the silicon-based material is coated with a hydrophilic polymer.

20. The neural interface of embodiment 1, wherein the first end portion, the second end portion and the center portion are each separated sufficiently to allow radial expansion and contraction of the target vessel without compressing nerves in the target vessel or reducing blood flow or fluid exchange with tissue of the target vessel.

21. The neural interface of embodiment 1, wherein the first electrode and the second electrode are single electrodes embedded in the flexible material.

22. The neural interface of embodiment 21, wherein the center portion includes a third electrode, wherein the third electrode is a single electrode embedded in the flexible material.

23. The neural interface of embodiment 1, wherein the first electrode and the second electrode are electrode arrays each having a plurality of individual electrodes, and wherein each individual electrode protrudes from the flexible material.

24. The neural interface of embodiment 23, wherein the center portion includes a third electrode array, and wherein each individual electrode protrudes from the flexible material.

25. The neural interface of embodiment 1, wherein the center portion is connected to the first end portion by a first spiral section and the center portion is connect to the second end portion by a second spiral section, wherein the center portion, the first spiral section and the first end portion are configured to complete a first helical turn around the target vessel in a first direction when the neural interface is positioned on the target vessel, wherein the center portion, the second spiral section and the second end portion are configured to complete a second helical turn around the target vessel in a second direction opposite the first direction when the neural interface is positioned on the target vessel.

26. The neural interface of embodiment 25, wherein a helix angle of the first helical turn and the second helical turn is less than 15 degrees.

27. The neural interface of embodiment 1, wherein the first electrode and the second electrode have a width of between 1 mm and 4 mm.

28. The neural interface of embodiment 1, wherein at least the first end portion is formed from a substantially opposing semi-circular arc, wherein the semi-circular arc includes a closed end attached to the spinal portion and an open end, wherein an opening is formed between the open end of the semi-circular arc substantially opposite the spinal portion, wherein the open end includes an attribution configured to engage a deployment tool, wherein application of pulling pressure on the deployment tool pulls the open end of the first end portion away from the spinal portion and enables the first end portion to be positioned around the target vessel, and wherein removal of the pulling pressure allows the first end portion to self-size to the surface of the target vessel.

29. The neural interface of embodiment 28, wherein the attribution is a protrusion.

30. The neural interface of embodiment 28, wherein the attribution is an opening formed in the flexible material.

31. The neural interface of embodiment 30, wherein the opening is configured to be engaged by suture wire of the deployment tool.

32. The neural interface of embodiment 1, wherein the first end portion and the second end portion are each formed from substantially opposing semi-circular arcs, wherein each semi-circular arc includes a closed end attached to the spinal portion and an open end, wherein an opening is formed between the open end of the semi-circular arc substantially opposite the spinal portion, wherein the open end includes an attribution configured to engage a deployment tool, further comprising a deployment tool configured to engage each attribution, wherein application of pulling pressure on the deployment tool pulls each open end away from the spinal portion and enables the first end portion and the second portion to be positioned around the target vessel, and wherein removal of the pulling pressure allows the first end portion and the second portion to self-size to the surface of the target vessel.

33. The neural interface of embodiment 1, wherein the attribution is an opening formed in the flexible material, wherein the deployment tool includes suture wire looped through each opening.

34. The neural interface of embodiment 33, wherein the deployment tool further includes a grab tab configured to enable a surgeon to apply the pulling pressure.

35. The neural interface of embodiment 34, wherein the grab tab includes silicone tubing through which the suture wire passes between the opening and a loop formed by the suture wire.

The embodiments of the present disclosure, while illustrated and described in terms of various embodiments, is not limited to the particular description contained in this specification. Additional alternative or equivalent components and elements may be readily used to practice the present disclosure.

What is claimed is:

1. A neural interface for interfacing with a target vessel, comprising:
   a first arm, a second arm, and a center portion positioned between the first arm and the second arm, wherein the first arm includes a first array of segmented individual electrodes and the second arm includes a second array of segmented individual electrodes, wherein the segmented individual electrodes of the first array and the segmented individual electrodes of the second array are each interconnected with the other segmented individual electrodes of their corresponding array via an interconnect, and wherein the first arm, the second arm and the center portion are each formed of a flexible material that is configured to enable each of the first arm, the second arm and the center portion to self-size to a surface of the target vessel when the neural interface is released at a position along the target vessel, and further wherein none of the first arm, the second arm nor the center portion form a closed circumscribed circular arc around the target vessel at any point along a length of the target vessel; and
   a spinal portion configured to house electrical conductors for the first electrode and the second electrode, the spinal portion being connected to one or more of the first arm, the center portion and the second arm,
   wherein the first electrode and the second electrode are embedded in the flexible material,
   wherein each of the first arm, the second arm and the center portion are configured to form an at least partially circular arc around the target vessel with at least one open end,
   wherein each of the first arm and the second arm include a deployment feature positioned near the at least one open end, wherein each deployment feature is configured to be griped by a deployment tool and pulled back to open each of the at least partially circular arcs formed by each of the first arm and the second arm, and enable the first arm and the second arm to be placed on the target vessel, and
   wherein the flexible material is biased to enable the first arm and the second arm to self-size to fit around the target vessel when the deployment tool releases each deployment feature.

2. The neural interface of claim 1, wherein the first electrode is positioned toward a surface of the first arm, such that in use the first electrode is positioned adjacent to an exterior surface of the target vessel, wherein the second electrode is positioned toward a surface of the second arm such that in use the second electrode is positioned adjacent to the exterior surface of the target vessel.

3. The neural interface of claim 1, wherein each of the first arm and the second arm are configured to form an at least partially circular arc around the target vessel, each of the at least partially circular arcs having two open ends, wherein the center portion is configured to form another at least partially circular arc around the target vessel, the another at least partially circular arc having one open end, a first closed end and a second closed end, wherein the first closed end is attached to the first arm at a first point and the second closed end is attached to the second arm at a second point, wherein a first section of the center portion between the first point and the one open end forms a first substantially full turn of a first helix, and wherein a second section of the center portion between the second point and the one open end forms a second substantially full turn of a second helix.

4. The neural interface of claim 1, wherein the first arm, the second arm and the center portion are formed from two substantially opposing at least partially circular arcs, wherein each at least partially circular arc includes a closed end attached to the spinal portion and an open end, wherein an opening is formed between the open end of each at least partially circular arc substantially opposite the spinal portion, wherein the center portion includes at least a third electrode attached to an electrical conductor housed by the spinal portion, wherein the third electrode is positioned toward an interior surface of the center portion.

5. The neural interface of claim 1, wherein each electrode is spaced a substantially constant distance from an adjacent electrode to provide a substantially uniform current density.

6. The neural interface of claim 1, wherein the flexible material is a silicon-based material.

7. The neural interface of claim 6, wherein the silicon-based material is doped with a steroid drug.

8. The neural interface of claim 6, wherein the silicon-based material is coated with a hydrophilic polymer.

9. The neural interface of claim 1, wherein the center portion includes a third electrode, wherein the third electrode is embedded in the flexible material.

10. The neural interface of claim 1, wherein each individual electrode protrudes from the flexible material.

11. The neural interface of claim 10, wherein the center portion includes a third electrode array, and wherein each individual electrode protrudes from the flexible material.

12. The neural interface of claim 1, wherein the interconnect is a microcoil.

13. A neural interface for interfacing with a target vessel, comprising:
- a first arm, a second arm, and a center portion positioned between the first arm and the second arm, wherein the first arm includes a first array of segmented individual electrodes and the second arm includes a second array of segmented individual electrodes, wherein the segmented individual electrodes of the first array and the segmented individual electrodes of the second array are each interconnected with the other segmented individual electrodes of their corresponding array via an interconnect, and wherein the first arm, the second arm and the center portion are each formed of a flexible material that is configured to enable each of the first arm, the second arm and the center portion to self-size to a surface of the target vessel when the neural interface is released at a position along the target vessel, and further wherein none of the first arm, the second arm nor the center portion form a closed circumscribed circular arc around the target vessel at any point along a length of the target vessel; and
- a spinal portion configured to house electrical conductors for the first electrode and the second electrode, the spinal portion being connected to one or more of the first arm, the center portion and the second arm,
- wherein the first electrode and the second electrode are embedded in the flexible material,
- wherein each of the first arm and the second arm are configured to form an at least partially circular arc around the target vessel, each of the at least partially circular arcs having two open ends, wherein the center portion is configured to form another at least partially circular arc around the target vessel, the another at least partially circular arc having one open end, a first closed end and a second closed end, wherein the first closed end is attached to the first arm at a first point and the second closed end is attached to the second arm at a second point, wherein a first section of the center portion between the first point and the one open end forms a first substantially full turn of a first helix, and wherein a second section of the center portion between the second point and the one open end forms a second substantially full turn of a second helix, and
- wherein the first arm and the second arm each include a deployment lumen positioned near the open ends, wherein each deployment lumen is configured to be griped by a deployment tool and pulled back to open each semi-circular arc and enable the first arm and the second arm to be placed on the target vessel, and wherein the flexible material is biased to enable the first arm and the second arm to self-size to fit around the target vessel when the deployment tool releases each deployment lumen.

14. The neural interface of claim 13, wherein each electrode is spaced a substantially constant distance from an adjacent electrode to provide a substantially uniform current density.

15. The neural interface of claim 13, wherein the flexible material is a silicon-based material.

16. The neural interface of claim 13, wherein the center portion includes a third electrode, wherein the third electrode is embedded in the flexible material.

17. A neural interface for interfacing with a target vessel, comprising:
- a first arm, a second arm, and a center portion positioned between the first arm and the second arm, wherein the first arm includes a first array of segmented individual electrodes and the second arm includes a second array of segmented individual electrodes, wherein the segmented individual electrodes of the first array and the segmented individual electrodes of the second array are each interconnected with the other segmented individual electrodes of their corresponding array via an interconnect, and wherein the first arm, the second arm and the center portion are each formed of a flexible material that is configured to enable each of the first arm, the second arm and the center portion to self-size to a surface of the target vessel when the neural interface is released at a position along the target vessel, and further wherein none of the first arm, the second arm nor the center portion form a closed circumscribed circular arc around the target vessel at any point along a length of the target vessel; and
- a spinal portion configured to house electrical conductors for the first electrode and the second electrode, the spinal portion being connected to one or more of the first arm, the center portion and the second arm,
- wherein the first electrode and the second electrode are embedded in the flexible material,
- wherein the first arm, the second arm and the center portion each form an at least partially circular arc around the target vessel with one open end and one closed end, wherein each of the one closed end is attached to the spinal portion, wherein the center portion includes at least a third electrode attached to an electrical conductor housed by the spinal portion,
- wherein the third electrode is positioned toward an interior surface of the center portion, and
- wherein the first arm and the second arm each include a deployment feature positioned near the open end, wherein each deployment feature is configured to be griped by a deployment tool and pulled back to open each at least partially circular arc and enable the first arm and the second arm to be placed on the target vessel, and wherein the flexible material is biased to enable the first arm and the second arm to self-size around the target vessel when the deployment tool releases each deployment feature.

18. The neural interface of claim 17, wherein each electrode is spaced a substantially constant distance from an adjacent electrode to provide a substantially uniform current density.

19. The neural interface of claim 17, wherein the flexible material is a silicon-based material.

20. The neural interface of claim 17, wherein the center portion includes a third electrode, wherein the third electrode is embedded in the flexible material.

* * * * *